(12) United States Patent
Rothschild et al.

(10) Patent No.: US 7,303,878 B2
(45) Date of Patent: *Dec. 4, 2007

(54) GENETIC MARKERS FOR IMPROVED MEAT CHARACTERISTICS IN ANIMALS (MC4R)

(75) Inventors: Max F. Rothschild, Ames, IA (US); Kwan Suk Kim, Ames, IA (US); Rebecca S. Emnett, Columbus, OH (US)

(73) Assignee: Iowa State University Research Foundation, Inc., Ames, IA (US)

( * ) Notice: Subject to any disclaimer, the term of this patent is extended or adjusted under 35 U.S.C. 154(b) by 471 days.

This patent is subject to a terminal disclaimer.

(21) Appl. No.: 10/816,304

(22) Filed: Apr. 1, 2004

(65) Prior Publication Data

US 2004/0261138 A1    Dec. 23, 2004

Related U.S. Application Data

(63) Continuation of application No. 09/538,165, filed on Mar. 30, 2000, now abandoned.

(51) Int. Cl.
*C12Q 1/68* (2006.01)
(52) U.S. Cl. .......................................... 435/6; 435/91.2
(58) Field of Classification Search ...................... None
See application file for complete search history.

(56) References Cited

U.S. PATENT DOCUMENTS 5,614,364 A    3/1997    Tuggle et al.

FOREIGN PATENT DOCUMENTS

| WO | WO 97 23644 A | 7/1997 |
| WO | WO 97 47316 A | 12/1997 |
| WO | WO 00/06777 | 2/2000 |

OTHER PUBLICATIONS

Thisted et al. May 25, 1998, obtained from http://www.stat.uchicago,edu/~thisted, pp. 1-6.*
Mummidi et al. The Journal of Biochemistry, 2000, vol. 275, No. 25, pp. 18946-18961.*
Lucentini. The Scientist, Dec. 20, 2004, p. 20.*
Hacker et al. Gut, 1997, vol. 40, pp. 623-627.*
Juppner. Bone. vol. 17, No. 2, supplement, Aug. 1995, pp. 39S-42S.*
Geller, Frank, et al. "Melanocortin-4 Receptor Gene Variant I103 is Negatively Associated with Obestity" Am. J. Hum. Genet. 74:572-581, 2004.
Kim, K.-S., et al. "Functional and Phylogenetic Analyses of a Melanocortin-4 Receptor Mutation in Domestic Pigs" Domestic Animal Endocrinology, 26 (2004) 75-86.
Nezer C. et al., "An imprinted QLT with major effect on muscle mass and fat deposition maps to the IGF2 locus in pigs", *Nature Genetics*, vol. 21, No. 2 (Feb. 1999) pp. 155-156 XP002204960.
Andersson, L., et al., "Genetic Mapping of quantitative trait loci for growth and fatness in pigs", *Science*, 263:1771-1774.
Gotoda, T., "Molecular screening of the human melanocortin-r receptor gene: identification of a missense variant showing no association with obesity, plasma glucose, or insulin", *Diabetologia* 40:976-979 (1997).
Kim, K-S, "A missense variant of the porcine melanocortin-4 receptor (MC4R) gene is associated with fatness, growth, and feed intake traits", *Mammalian Genome*, 11:131-135 (2000).
Unruh, J.A., "The influence of genotype, sex, and dietary lysine on Pork subprimal cut yields and carcass quality of pigs fed to either 104 or 127 kilograms", *J. Anim. Sci.* 74:1274-1283 (1996).
Wood, J.D., "Animal nutrition and metabolism group symposium on improving meat production for future needs", *Proceedings of the Nutrition Society* 58:363-370 (1999).

* cited by examiner

*Primary Examiner*—Juliet C. Switzer
(74) *Attorney, Agent, or Firm*—McKee, Voorhees & Sease, P.L.C.

(57) ABSTRACT

Genetic markers in the porcine melanocortin-4 receptor (MC4R) gene are disclosed which are associated with favorable meat quality traits including, drip loss, marbling, pH and color. Further, novel sequence data from regions of the gene are disclosed which may be used in a PCR test to screen for the presence of the marker. The genetic marker may be used to screen animals for breeding purposes which have the desired traits. Kits which take advantage of the PCR test are also disclosed.

1 Claim, 13 Drawing Sheets

```
  1  ACAAGAATCT GCATTCACCC ATGTACTTTT TCATCTGTAG CCTGGCTGTG
 51  GCTGATATGC TGGTGAGCGT TTCCAATGGG TCAGAAACCA TTGTCATCAC
101  CCTATTAAAC AGCACGGACA CGGACGCACA GAGTTTCACA GTGAATATTG
151  ATAATGTCAT TGACTCAGTG ATCTGTAGCT CCTTACTCGC CTCAATTTGC
201  AGCCTGCTTT CGATTGCAGT GGACAGGTAT TTTACTATCT TTTATGCTCT
251  CCAGTACCAT AACATTATGA CAGTTAAGCG GGTTGGAATC ATCATCAGTT
301  GTATCTGGGC AGTCTGCACG GTGTCGGGTG TTTTGTTCAT CATTTACTCA
351  GATAGCAGTG CTGTTATTAT CTGCCCTCATA ACCGTGTTCT TCACCATGCT
401  GGCTCTCATG GCTTCTCTCT ATGTCCACAT GTTCCCTCATG GCCAGACTCC
451  ACATTAAGAG GATCGCCGTC CTCCCAGGCA CTGGCACCAT CCGCCAAGGT
501  GCCAACATGA AGGGGGCAAT TACCCTGACC ATCTTGATTG GGGTCTTTGT
551  GGTCTGCTGG GCCCCCTTCT TCCTCCACTT AATATTCTAT ATCTCCTGCC
```

*Fig. 1*

601  CCCAGAATCC ATACTGTGTG TGCTTCATGT CTCACTTTAA TTTGTATCTC
651  ATCCTGATCA TGTGTAATTC CATCATCXAT CCCCTGATTT ATGCACTCCG
701  GAGCCAAGAA CTGAGGAAAA CCTTCAAAGA GATCATCTGT TGCTAT

Fig. 1A

```
                              10                20                30
con-mc4r.seq         ACAAGAATCTGCATTCACCCATGTACTTTT
                     ||||||||||||||||||||||||||||||
s77415               ACAAGAATCTGCATTCACCCATGTACTTTT
                              610               620               630

40                50                60                70                80                90
con-mc4r.seq         ATATCTTAGTGATTGTGGCAATAGCCAAGAATCTTGATATGCTGGTGAGCGTTTCCAATGGGTCAGAAACCA
                     |||||| ||||| ||||||||||||  ||||| |||||||||||||||||||||||||||  ||||||||||
s77415               TCATCTGTAGCCTGGCTGGCTGTGCTGATATGCTGGTGAGCGTTTCCAATGGGTCAGAAACCA
                              580               590               600               610 con-mc4r.seq         TCATCTGCAGCTTGGCTGTGTGGCTGATATGCTGGTGAGCGTTTCAAATGGATCAGAAACCA
                     |||||||||||||||||||  ||||||||||||||||||||| |||||||| ||||||||||
s77415               TCATCTGCAGCTTGGCTGTGTGGCTGATATGCTGGTGAGCGTTTCAAATGGATCAGAAACCA
                              640               650               660               670               680               690

100               110               120               130               140               150
con-mc4r.seq         TTGTCATCACCCTATTAAACAGCAGACGGACACGGACGCACAGAGTTTCACAGTGAATATTG
                     || |||||||||||||||||||| || ||||| |||||||||||||||||||||||||||||
s77415               TTATCATCACCCTATTAAACAGCAGACTCGTGATCAGACAGATACGGATGCACAGAGTTTCACAGTGAATATTG
                              700               710               720               730               740               750

160               170               180               190               200               210
con-mc4r.seq         ATAATGTCATTGACTCAGTGATCTGTAGCTCCTTACTCTGCCTCAATTTGCAGCCTGCTTT
                     ||||||||||||||||||||||||||||||||||||||||| |||| || ||||||||||||
s77415               ATAATGTCATTGACTCGGTGATCTGTAGCTCCCTTGCATCCATTGCTTGCAGCCTGCTTT
                              760               770               780               790               800               810
```

*Fig. 2A*

```
con-mc4r.seq  CGATTGCAGTGGACAGGTATTTACTATCTTTATGCTCTCCAGTACCATAACATTATGA
              ||||||||||||||||||| |||||||||||| ||||||| |||||||||||||||||
s77415        CAATTGCAGTGGACAGGTACTTTACTATCTTCTATGCTCTCCAGTACCATAACATTATGA
              820       830       840       850       860       870 con-mc4r.seq  CAGTTAAGCGGGTTGGAATCATCATCAGTTGTATCTGGGCAGTCTGCACGGTGTCGGGTG
              |||||||||||||||||| ||||||| |||||||||||||||||||| |||||||
s77415        CAGTTAAGCGGGTTGGGATCAGCATAAGTTGTATCTGGGCAGCTTGCACGGTTTCAGGCA
              880       890       900       910       920       930 con-mc4r.seq  TTTTGTTCATCATTACTCAGATAGCAGTGCTGTTATTATCTGCCTCATAACCGTGTTCT
              |||||||||||||||||||||||||| |||||||| ||| || ||||||||||||||||
s77415        TTTTGTTCATCATTACTCAGATAGTAGTGCTGTGTGCTGTGTCCTCATCATCCATGTTCT
              940       950       960       970       980       990 con-mc4r.seq  TCACCATGCTGGCTCTCATGGCTTCTCTATGTCCACATGTTCCTCATGGCCAGACTCC
              ||||||||||||||||||||||||||||||||||||||||||||||||| |||||||||
s77415        TCACCATGCTGGCTCTCATGGCTTCTCTCTATGTCCACATGTTCCTGATGGCCAGGCTTC
              1000      1010      1020      1030      1040      1050 con-mc4r.seq  ACATTAAGAGAGGATCGCCGTCCTCCCAGGCACTGGCACCATCCGGCCAAGGTGCCAACATGA
              |||||||||||||||| || ||||||||| ||||||||||||||||||||||||||| |||
s77415        ACATTAAGAGAGGATTGCTGTCTCCTCCCCGGCACTGGTGCCATCCGGCCAAGGTGCCAATATGA
              1060      1070      1080      1090      1100      1110
```

*Fig. 2B*

```
con-mc4r.seq  AGGGGGCAATTACCCTGACCATCTTGATTGGGGTCTTTGTGGTCTCGCTGGGCCCCTTCT
              ||||||||||||||||||||||||||||||||||||||||||||||||||||||||||||
s77415        AGGGGAGCGATTACCTTGACCATCCTGATTGGCGTCTTTGTTCTGCTGGGCCCCATTCT
              1120      1130      1140      1150      1160      1170 con-mc4r.seq  TCCTCCACTTAATATTCTATATCTCCTGCCCCCAGAATCCATACTGTGTGCTTCATGT
              ||||||||||||||||||||||||||  ||  ||||||||||||||||||||||||||
s77415        TCCTCCACTTAATATTCTACATCTCTTGTCCTCAGAATCCATATTGTGTGCTTCATGT
              1180      1190      1200      1210      1220      1230 con-mc4r.seq  CTCACTTTAATTTGTATCTCATCCTGATCATGTGTAATTCCATCATCAATCCCCTGATTT
              |||||||| ||||||||||||||||||||||||||||||||||||||||| ||||||||
s77415        CTCACTTTAACTTGTATCTCATACTGATCATGTGTAATTCCATCATCGATCCTCTGATTT
              1240      1250      1260      1270      1280      1290 con-mc4r.seq  ATGCACTCCGGAGCCAAGAACTGAGGAAAACCTTCAAAGAGATCATCTGTTGCTAT
              ||||||||||||||||||||||||||||||||||||||||||||||||||||||||
s77415        ATGCACTCCGGAGTCAAGAACTGAGGAAAACCTTCAAAGAGATCATCTGTTGCTATCCCC
              1300      1310      1320      1330      1340      1350 s77415        TGGGAGGCCTTTGTGTGACTTGTCTAGCAGATATTTAAATGGGGACAGAGCACGCAATATAGG
              1360      1370      1380      1390      1400      1410
```

Fig.2C

```
human.pep      QLFVSPEVFVTLGVISLLENILVIVAIAKNKNLHSPMYFFICSLAVADMLVSVSNGSETI
                                          ||||||||||||||||||||||||||||||
mc4r-allel                                KNLHSPMYFFICSLAVADMLVSVSNGSETI
               50        60        70        80        90        100
                                                                     30
                                                    10        20 human.pep      IITLLNSTDTDAQSFTVNIDNVIDSVICSSLLASICSLLSIAVDRYFTIFYALQYHNIMT
               :||||||||||||||||||||||||||||||||||||||||||||||||||||||||||
mc4r-allel     VITLLNSTDTDAQSFTVNIDNVIDSVICSSLLASICSLLSIAVDRYFTIFYALQYHNIMT
               110       120       130       140       150       160
                40        50        60        70        80        90 human.pep      VKRVGISISCIWAACTVSGILFIIYSDSSAVIICLITMFFTMLALMASLYVHMFLMARLH
               |||||  ||||||| |||||:|||||||||||||||||||||||||||||||||||||||
mc4r-allel     VKRVGIIISCIWAVCTVSGVLFIIYSDSSAVIICLITVFFTMLALMASLYVHMFLMARLH
               170       180       190       200       210       220
               100       110       120       130       140       150 human.pep      IKRIAVLPGTGAIRQGANMKGAITLTILIGVFVVCWAPFFLHLIFYISCPQNPYCVCFMS
               ||||||||||| ||||||||||||||||||||||||||||||||||||||||||||||||
mc4r-allel     IKRIAVLPGTGTIRQGANMKGAITLTILIGVFVVCWAPFFLHLIFYISCPQNPYCVCFMS
               230       240       250       260       270       280
               160       170       180       190       200       210 human.pep      HFNLYLILIMCNSIIDPLIYALRSQELRKTFKEIICCYPLGGLCDLSSRY
               |||||||||||||||||||||||||||||||||||||||||
mc4r-allel     HFNLYLILIMCNSIIDPLIYALRSQELRKTFKEIICCY
               290       300       310       320       330
               220       230       240
```

Fig. 3A

```
human.pep     QLFVSPEVFVTLGVISLLENILVIVAIAKNKNLHSPMYFFICSLAVADMLVSVSNGSETI
              :::::::::::::::
mc4r-alle2                             KNLHSPMYFFICSLAVADMLVSVSNGSETI
                   50        60        70        80        90       100
                                                 10        20        30 human.pep     IITLLNSTDTDAQSFTVNIDNVIDSVICSSLLASICSLLSIAVDRYFTIFYALQYHNIMT
              :|:::|||||||||||||||||||||||||||||||||||||||||||||||||||||||
mc4r-alle2    VITLLNSTDTDAQSFTVNIDNVIDSVICSSLLASICSLLSIAVDRYFTIFYALQYHNIMT
                  110       120       130       140       150       160
                   40        50        60        70        80        90 human.pep     VKRVGISISCIWAACTVSGILFIIYSDSSAVIICLITMFFTMLALMASLYVHMFLMARLH
              ||||||:|||||:|||||:|||||||||||||||||||:|||||||||||||||||||||
mc4r-alle2    VKRVGIIISCIWAVCTVSGVLFIIYSDSSAVIICLITVFFTMLALMASLYVHMFLMARLH
                  170       180       190       200       210       220
                  100       110       120       130       140       150 human.pep     IKRIAVLPGTGAIRQGANMKGAITLTILIGVFVVCWAPFFLHLIFYISCPQNPYCVCFMS
              ||||||||||:|:|||||||||||||||||||||||||||||||||||||||||||||||
mc4r-alle2    IKRIAVLPGTGTIRQGANMKGAITLTILIGVFVVCWAPFFLHLIFYISCPQNPYCVCFMS
                  230       240       250       260       270       280
                  160       170       180       190       200       210 human.pep     HFNLYLILIMCNSIIDPLIYALRSQELRKTFKEIICCYPLGGLCDLSSRY
              ||||||||||||||:|:|||||||||||||||||||||||
mc4r-alle2    HFNLYLILIMCNSIINPLIYALRSQELRKTFKEIICCY
                  290       300       310       320       330
                  220       230       240
```

*Fig. 3B*

S0082    MC4R   rec. fracs.=   0.05,   lods =   14.74

CGA      MC4R   rec. fracs.=   0.14,   lods =    6.88

S0020    MC4R   rec. fracs.=   0.18,   lods =    5.32

S0079    MC4R   rec. fracs.=   0.12,   lods =   10.35

S0155    MC4R   rec. fracs.=   0.14,   lods =    7.68

S0122    MC4R   rec. fracs.=   0.18,   lods =    5.17

S0313    MC4R   rec. fracs.=   0.00,   lods =   17.76

S0312    MC4R   rec. fracs.=   0.20,   lods =    5.60

S0311    MC4R   rec. fracs.=   0.17,   lods =    7.18

S0416    MC4R   rec. fracs.=   0.20,   lods =    3.21

S0331    MC4R   rec. fracs.=   0.02,   lods =   21.91

S0396    MC4R   rec. fracs.=   0.16,   lods =    7.85

BHT0433  MC4R   rec. fracs.=   0.02,   lods =   21.32

S0536    MC4R   rec. fracs.=   0.03,   lods =   15.61

CAPN3    MC4R   rec. fracs.=   0.12,   lods =    6.65

*Fig. 4A*

| | | | | | | |
|---|---|---|---|---|---|---|
| KGF | MC4R | rec. fracs.= | 0.09, | lods = | 6.46 | |
| MEF2A | MC4R | rec. fracs.= | 0.05, | lods = | 14.36 | |
| MC4R | MC4R | rec. fracs.= | 0.00, | lods = | 26.19 | |
| S0082 | MC4R | rec. fracs.= | 0.00, | 0.09, | lods = | 15.86 |
| CGA | MC4R | rec. fracs.= | 0.07, | 0.22, | lods = | 7.46 |
| S0020 | MC4R | rec. fracs.= | 0.00, | 0.25, | lods = | 6.33 |
| S0079 | MC4R | rec. fracs.= | 0.00, | 0.19, | lods = | 11.48 |
| S0155 | MC4R | rec. fracs.= | 0.00, | 0.24, | lods = | 9.98 |
| S0122 | MC4R | rec. fracs.= | 0.00, | 0.27, | lods = | 7.10 |
| S0313 | MC4R | rec. fracs.= | 0.00, | 0.00, | lods = | 17.76 |
| S0312 | MC4R | rec. fracs.= | 0.04, | 0.29, | lods = | 7.45 |

Fig. 4B

| S0311 | MC4R | rec. fracs.= | 0.00 | 0.28, | lods = | 9.02 |
|---|---|---|---|---|---|---|
| S0416 | MC4R | rec. fracs.= | 0.00 | 0.31, | lods = | 4.17 |
| S0331 | MC4R | rec. fracs.= | 0.05 | 0.00, | lods = | 22.14 |
| S0396 | MC4R | rec. fracs.= | 0.03 | 0.24, | lods = | 9.33 |
| BHT0385 | MC4R | rec. fracs.= | 0.14 | 0.36, | lods = | 3.46 |
| BHT0433 | MC4R | rec. fracs.= | 0.05 | 0.00, | lods = | 21.82 |
| S0536 | MC4R | rec. fracs.= | 0.00 | 0.05, | lods = | 15.77 |
| CAPN3 | MC4R | rec. fracs.= | 0.00 | 0.18, | lods = | 7.35 |
| KGF | MC4R | rec. fracs.= | 0.00 | 0.17, | lods = | 6.74 |
| MEF2A | MC4R | rec. fracs.= | 0.10 | 0.00, | lods = | 14.52 |
| MC4R | MC4R | rec. fracs.= | 0.00 | 0.00, | lods = | 26.19 |

Fig. 4C

| | | | | |
|---|---|---|---|---|
| 0 | ESR | | | 0.0 |
| | | 0.18 | 18.4 | |
| 1 | S0008 | | | 18.4 |
| | | 0.12 | 11.9 | |
| 7 | CGA | | | 30.3 |
| | | 0.03 | 2.8 | |
| 3 | S0312 | | | 33.1 |
| | | 0.05 | 4.9 | |
| 4 | S0122 | | | 38.1 |
| | | 0.09 | 9.4 | |
| 8 | KGF | | | 47.4 |
| | | 0.06 | 5.8 | |
| 6 | CAPN3 | | | 53.2 |
| | | 0.02 | 2.5 | |
| 9 | MEF2A | | | 55.7 |
| | | 0.06 | 6.1 | |
| 5 | MC4R | | | 61.8 |
| | | 0.06 | 5.6 | |
| 10 | S0313 | | | 67.4 |
| | | 0.00 | 0.0 | |
| 11 | S0082 | | | 67.4 |
| | | 0.03 | 3.4 | |
| 12 | S0079 | | | 70.8 |
| | | 0.03 | 2.5 | |
| 14 | S0142 | | | 73.3 |
| | | 0.01 | 1.0 | |
| 13 | S0020 | | | 74.4 |
| | | 0.04 | 4.3 | |
| 15 | S0311 | | | 78.7 |
| | | 0.00 | 0.0 | |
| 16 | S0155 | | | 78.7 |
| | | 0.12 | 12.2 | |
| 17 | S0113 | | | 90.9 |
| | | 0.20 | 21.0 | |
| 18 | S0302 | | | 111.9 |
| | | 0.22 | 23.4 | |
| 19 | S0112 | | | 135.3 |

Fig. 4D

| pMC4R | ......MSHFNLYLILIMCNSIIDPLIYAL......* |
|---|---|
| hMC4R | ......MSHFNLYLILIMCNSIIDPLIYAL......304 |
| rMC4R | ......MSHFNLYLILIMCNAVIDPLIYAL......304 |
| sheep MC5R | ......MSHFNMYLILIMCNSVIDPLIYA........286 |
| bovine MC5R | ......MSHFNMYLILIMCNSVIDPLIYA........286 |
| bovine MC2R | ......MSLFQVNGVLIMCNAIIDPFIYAL......268 |
| hMC3R | ........AHFNTYLVLIMCNSVIDPLIYA........327 |
| mMC3R | ........AHFNTYLVLIMCNSVIDPLIYA........290 |
| hMC2R | ......MSHFNMYLILIMCNSVMDPLIYA........268 |
| hMC1R | ........SYFNLFLILIICNSVVDPLIYA........299 |
| bEDG-2R | ......LAYEKFFLLLAEFNSAMNPIIYSYR....314 |
| hEDG-4R | ...............FLLLAEANSLVNAAVYSCR....298 |
| human cannab | ...........VFAFCSMLCLLNSTVNPLIYAL......399 |
| hH2AB | ............FQFFFWIGYCNSSLNPVIYTI......290 |
| rSSR2 | ............FDFVVILTYANSCANPILYAFL....315 |
| hGAL1-R | ........................LAYSNSSVNPIIYAFL....306 |

*Fig. 6*

GENETIC MARKERS FOR IMPROVED MEAT CHARACTERISTICS IN ANIMALS (MC4R)

CROSS-REFERENCE TO RELATED APPLICATIONS

This application is a continuation of U.S. patent application Ser. No. 09/538,165 filed on Mar. 30, 2000, now abandoned the contents of which are hereby incorporated by reference in their entirety.

GRANT REFERENCE CLAUSE

This invention was supported at least in part by grants from the United States Department of Agriculture through the Iowa Agriculture and Home Economics Experiment Station (IAHEES) and Project Number IOW03148 (Hatch Funds). The United States government may have certain rights in this invention.

FIELD OF THE INVENTION

The present invention relates to a method of genetically evaluating animals by assaying for the presence of at least one genetic marker which is indicative of one or more traits associated with meat quality. In particular, the method analyzes for variation in the melanocortin-4 receptor (MC4R) gene or other variations associated therewith which are indicative of these favorable traits.

BACKGROUND OF THE INVENTION

Genetic differences exist among individual animals as well as among breeds which can be exploited by breeding techniques to achieve animals with desirable characteristics. For example, Chinese breeds are known for reaching puberty at an early age and for their large litter size, while American breeds are known for their greater growth rates and leanness. Often, however, heritability for desired traits is low, and standard breeding methods which select individuals based upon phenotypic variations do not take fully into account genetic variability or complex gene interactions which exist.

Restriction fragment length polymorphism (RFLP) analysis has been used by several groups to study pig DNA. Jung et al., *Theor. Appl. Genet.*, 77:271-274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26-28, 1990, incorporated herein by reference, reports on the polymorphism of swine major histocompatibility complex (MHC) genes for Chinese pigs, also demonstrated by RFLP analysis. Jung et al., *Theor. Appl. Genet.*, 77:271-274 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526 issued to Rothschild et al. disclose a polymorphism in the pig estrogen receptor gene which is associated with larger litter size, the disclosure of which is incorporated herein by reference.

U.S. Pat. No. 5,935,784 discloses polymorphic markers in the pig prolactin receptor gene which are associated with larger litter size and overall reproductive efficiency. Perhaps one of the most important characteristics for any meat producing animal is meat quality. Meat quality is a difficult characteristic to assess, as many different aspects, both objective and subjective, make up the overall trait. The list of factors which determine quality in meat, as with other foods, is rather long (Wood et al., Proceedings of The Nutrition Society (1999) 58:363-70). It includes freedom from microbiological hazards (food safety) and prevention of animal exploitation (animal welfare). It also includes the sensory appeal of meat, i.e. its taste or eating quality, and perceived healthiness, especially in relation to the amount and type of fat.

The quality of raw pig meat is influenced by a large number of genetic and non-genetic factors. The latter include farm, transport, slaughter and processing conditions. Meat scientists have performed a substantial amount of research on these factors, which has led to considerable quality improvement. Part of the research has also been dedicated to the genetic background of the pigs, and several studies have revealed the importance of genetic factors. This has made the industry aware that selective breeding of pigs and the use of gene technology can play an important role in enhancing pork quality.

Information at DNA level can help to fix a specific major gene, but it can also assist the selection of quantitative trait for which we already select. Molecular information in addition to phenotypic data can increase the accuracy of selection and therefore the selection response. The size of the extra response in such a Marker Assisted Selection (MAS) program has been considered by many workers from a theoretical point of view. In general terms, MAS is more beneficial for traits with a low heritability and which are expensive to measure phenotypically. Meat quality in particular qualifies as an excellent opportunity to utilize MAS. For example, Meuwissen, T. H. E. and Goddard, M. E. (1996) "The use of Marker Haplotypes in Animal Breeding Schemes", Genet. Sel. Evol., 28 161-176 considered the impact of Marker Assisted Selection for traits such as reproduction and meat quality that are difficult to progress using traditional methods. their results are extremely encouraging, showing that for traits such as meat quality, where the trait is measured after slaughter, an additional response of up to 64% could be achieved.

Indeed, the best approach to genetically improve meat quality is to find relevant DNA-markers directly in the population under selection. Meat quality measurements can be performed continuously on some animals from the nucleus populations of breeding organizations. Since a full assessment of meat quality can only be done after slaughter, the data must be collected on culled animals and cannot be obtained on potential breeding animals.

This phenotypic meat quality data is collected in order to enable the detection of relevant DNA markers, and to validate markers from experimental populations or to test candidate genes. Significant markers or genes can then be included directly in the selection process. An advantage of the molecular information is that we can obtain it already at very young age of the breeding animal, which means that animals can be preselected based on DNA markers before the growing performance test is completed. This is a great advantage for the overall testing and selection system.

It can be seen from the foregoing that a need exists for a method for improving meat quality characteristics in animals by identifying and selecting animals with the improved meat characteristics.

An object of the present invention is to provide a genetic marker based on or within the MC4R gene which is indicative of favorable meat characteristics such as those evidenced by pH, marbling, color and drip loss.

Another object of the invention is to provide an assay for determining the presence of this genetic marker.

A further object of the invention is to provide a method of evaluating animals that increases accuracy of selection and breeding methods for the desired traits.

Yet another object of the invention is to provide a PCR amplification test which will greatly expedite the determination of presence of the marker.

An additional object of the invention is to provide a kit for evaluating a sample of animal DNA for the identified genetic marker.

These and other objects, features, and advantages will become apparent after review of the following description and claims of the invention which follow.

SUMMARY OF THE INVENTION

This invention relates to the discovery of a polymorphism within the melanocortin-4 receptor (MC4R) gene which is associated with meat quality traits in animals. This gene is highly conserved among species and it is expected that the different alleles disclosed herein will also correlate with variability in this gene in other meat producing animals such as bovine, sheep, chicken, etc. This polymorphic site has been previously described in an earlier patent application PCT/US99/16862, publication number WO 00/06777 the disclosure of which is incorporated herein. In the earlier application this site was found to significantly correlate with weight gain and feed intake, in other words, traits involving growth rate of the pig. Surprisingly, as fast growth is generally considered to be negatively correlated with meat quality, the marker has now been shown to correlate with favorable meat characteristics such as pH level, marbling, color, and drip loss. These multigenic characteristics have been previously difficult to associate with quantitative trait loci and current improvements in meat characteristics have centered around understanding and controlling the numerous factors i.e. on a farm, transport, and/or slaughter plant handling influencing meat quality including the incidence of PSE (pale, soft, exudative), RSE (red, soft, exudative), and DFD (dark, firm, dry) meat. According to the invention, the association of the MC4R polymorphism with the these trait(s) enables genetic markers to be identified for specific breeds or genetic lines to identify animals with favorable meat characteristics early in the animal's life.

The marker genotype consists of a polymorphism within the MC4R gene that results in a guanine to adenine transition and a missense mutation of aspartic acid(D) codon (GAU) into asparagine(N) codon (AAU) at a position corresponding to amino acid position 298 of the human MC4R protein resulting in a TaqI restriction site in one allele of the gene. In one embodiment of the invention a TaqI restriction pattern which identifies the polymorphism is used to assay for the presence or absence of markers associated with the desirable meat traits. The invention includes assays for detection of the marker, or markers linked thereto as well as the sequence characterization of the polymorphism and includes novel sequences in the MC4R gene which may be used to design amplification primers for such an assay (SEQ ID NO:1). Additionally, the invention includes a method for using the assay in breeding programs for animal selection and a kit for performing the assay.

BRIEF DESCRIPTION OF THE DRAWINGS

FIGS. 1-1A are the sequence listing for MC4R in pigs (SEQ ID NO:1). "X" represents the site of the polymorphism.

FIGS. 2A-2C represent a comparison of the DNA sequence between the human (SEQ ID NO:2) and the porcine (SEQ ID NO:1) MC4R gene.

FIGS. 3A-3B represent a comparison of the amino acid sequence between the human (SEQ ID NO:3) and the porcine (SEQ ID NO:4) MC4R gene.

FIGS. 4a, 4b, 4c and 4d are linkage reports for MC4R from CRI-MAP.

FIG. 6 depicts multiple-alignments of the putative seventh transmembrane domain of porcine MC4R with other MCRs and GPCRs. (SEQ ID NOS:11-26). The "*" represents the predicted sequence positions for porcine MC4R. The other amino acid sequences were obtained from the GenBank database (accession numbers P32245, P70596, P41983, P56451, P34974, P41968, P33033, Q01718, Q01726, Q28031, AF011466, P21554, P18089, P30680, P47211). The missense variant in porcine MC4R substituted amino acid N for D in the position marked with an arrow. The Asp (D) residue is highly conserved among MCRs, and the Asn (N) residue is well conserved in most other GPCRs.

DETAILED DESCRIPTION OF THE INVENTION

Figure 5:
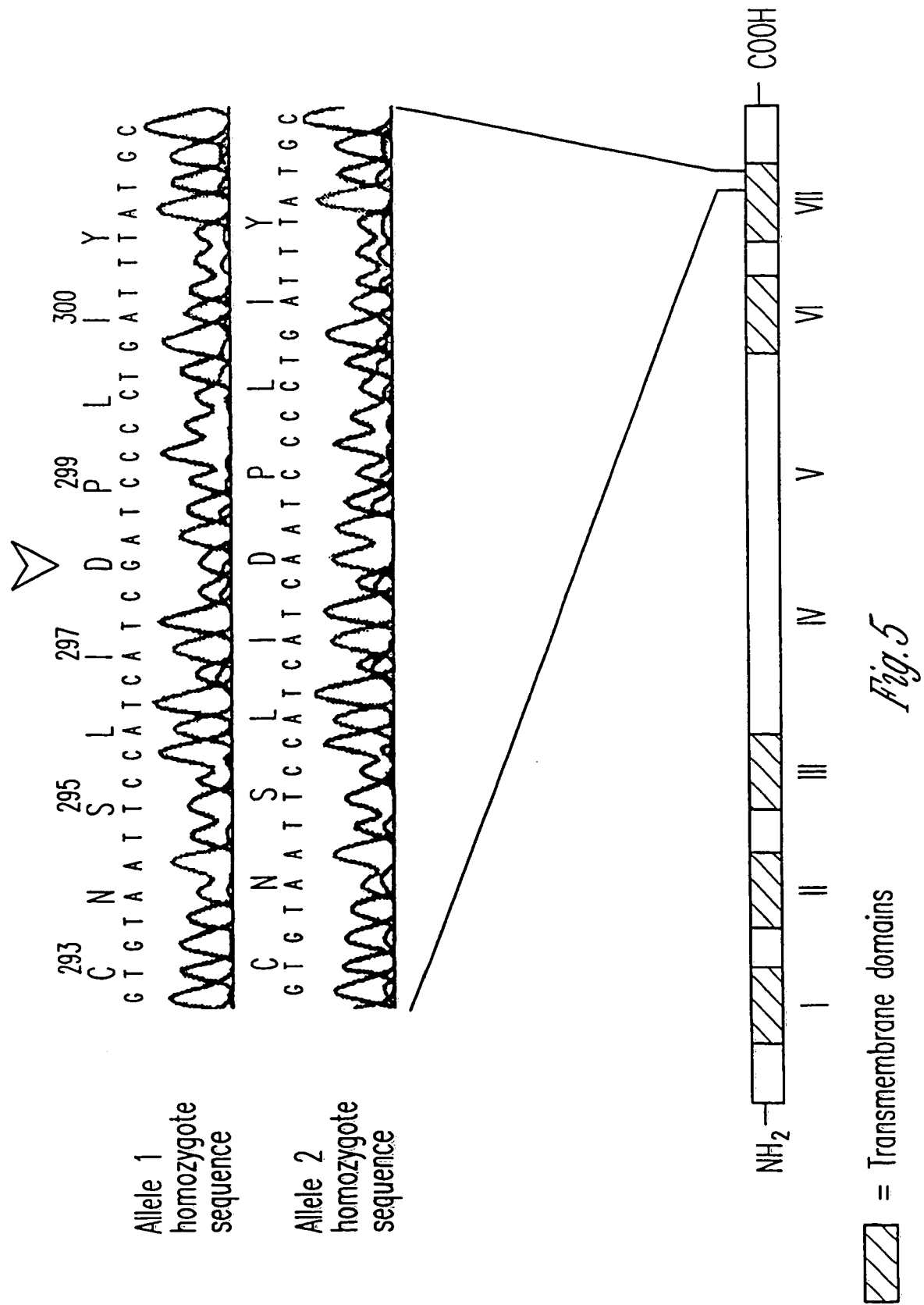
FIG. 5 depicts partial nucleotide and amino acid sequences (SEQ ID NOS:27-29) of the porcine MC4R gene. The amino acid translation shows an amino acid substitution at codon 298.

The melanocortin-4 receptor (MC4R) has been shown to be an important mediator of long term weight homeostasis. MC4R antagonists can increase food intake and body weight during chronic administration. Skuladottir, G. V., et al., "Long term orexigenic effect of a novel melanocortin 4 receptor selective antagonist", *British J. of Pharm.*, 126(1): 27-34 (1999).

Lu et al., *Nature* (Oct. 27, 1994), 371 (6500):799-802 suggested that the melanocortin receptors are involved in controlling food intake and energy balance through studying its antagonism to the agouti obesity syndrome. Huszar et al., *Cell* (Jan. 10, 1997) 88(1):131-41 found that inactivation of the melanocortin-4 receptor gene (MC4R) resulted in a maturity onset obesity syndrome in mice and demonstrated a major role of MC4R protein in the regulation of energy balance related to the agouti obesity syndrome. In addition, the MC4R protein mediates the effects of leptin, one of the important signaling molecules in energy homeostasis (Seeley et al. 1997).

According to the present invention, a variant or polymorphism in the MC4R gene has been located, and this genetic variability is associated with phenotypic differences in the porcine meat quality traits as evidenced by pH, marbling, color and drip loss.

In one embodiment of the invention, an assay is provided for detection of presence of a desirable genotype in animals. The assay involves assaying the genomic DNA purified from blood, tissue, semen, or other convenient source of genetic material by the use of primers and standard techniques, such as the polymerase chain reaction (PCR), then digesting the DNA with a restriction enzyme (e.g., Taq I or other enzyme which cleaves at the same G→A site) so as to yield gene fragments of varying lengths, and separating at least some of the fragments from others (e.g., using electrophoresis).

The fragments may also be detected by hybridizing with a nucleotide probe (e.g., radio-labeled cDNA probes) that contains all or at least a portion of the MC4R gene cDNA sequence to the separated fragments and comparing the results of the hybridization with assay results for a gene sequence known to have the marker or a sequence known to not have the marker. Selection and use of probes for detection of MC4R sequences based on the known and disclosed MC4R sequences is generally known to those skilled in the art. The probe may be any sequence which will hybridize to the separated digestion products and allow for detection.

Another embodiment of the invention provides a kit for assaying the presence in a MC4R gene sequence of a genetic marker. The marker being indicative of heritable traits of meat quality characteristics. The kit in a preferred embodiment also includes novel PCR primers comprising 4-30 contiguous bases on either side of the polymorphism to provide an amplification system allowing for detection of the G→A Transition polymorphism by PCR digestion of PCR products. The sequence surrounding the polymorphic site is shown in SEQ ID NO:1, FIG. 1. Several primers have also been disclosed including SEQ ID NOS:5 and 6, SEQ ID NOS:9 and 10 and mapping primers 7 and 8. The preferred primers are SEQ ID NO:9 and SEQ ID NO:10.

A further embodiment comprises a breeding method whereby an assay of the above type is conducted on a plurality of DNA samples from different animals or animal embryos to be selected from and based on the results, certain animals are either selected or dropped out of the breeding program.

According to the invention, in a preferred embodiment, the polymorphism in the MC4R gene identifiable by the Taq I restriction pattern, is disclosed. As is known in the art, restriction patterns are not exact determinants of the size of fragments and are only approximate. When the primers SEQ ID NOS:5 and 6 are used the polymorphism is identifiable by three bands from a Taq I digestion of the PCR product, 466, 225, and 76 base pairs (bp) for one homozygous genotype (allele 1); two bands, 542 and 225 bp for another homozygous genotype (allele 2); and four bands for the heterozygous genotype (542, 466, 225, and 76 bp). When the preferred primers are used, SEQ ID NOS:9 and 10 the bands upon Tag I digestion include 156 and 70 bp for allele 1 and one 226 bp fragment for allele 2. Those of skill in the art will appreciate that the design of alternate primers PCR conditions and restriction patterns for identifying the presence of allele 2 using the MC4R sequence data herein or other data for closely linked loci represent nothing more than routine optimization of parameters and are intended to be within the scope of the invention. The marker for improved meat characteristics as evidenced by all four meat quality measurements observed herein (allele 2). The allele 2 genotype was previously associated with faster growth rate. This is surprising because the current state of the art concluded that there is a negative correlation between growth rate and meat quality.

In addition, the polymorphism associated with the pattern has been identified at the nucleotide level. The polymorphic Taq I site was sequenced along with the general surrounding area. See SEQ ID NO: 1. The sequences surrounding the polymorphism have facilitated the development of a PCR test in which a primer of about 4-30 contiguous bases taken from the sequence immediately adjacent to the polymorphism is used in connection with a polymerase chain reaction to greatly amplify the region before treatment with the Taq I restriction enzyme. The primers need not be the exact complement; substantially equivalent sequences are acceptable.

From sequence data, it was observed that in allele 2 a guanine is substituted with an adenine at position 678 of the PCR product shown in FIG. 1 or at position 298 of the analogous human MC4R amino acid of the MC4R protein changing the aspartic acid codon (GAU) into an asparagine codon (AAU). The PCR test for the polymorphism used a forward primer of 5'-TGG CAA TAG CCA AGA ACA AG-3' (SEQ ID NO:5) and a reverse primer of 5'-CAG GGG ATA GCA ACA GAT GA-3' (SEQ ID NO:6). Pig specific primers used for physical mapping were a forward primer of 5'-TTA AGT GGA GGA AGA AGG-3' (SEQ ID NO:7) and a reverse primer of 5'-CAT TAT GAC AGT TAA GCG G-3' (SEQ ID NO:8). The resulting amplified product of about 750 bp, when digested with Taq I, results in allelic fragments of 466, 225, and 76 bp (allele 1) or 542 and 225 bp (allele 2). The most preferred primers resulting in either 2 or 1 fragment after Taq I digestion are SEQ ID NOS:9 and 10. Allele 1 generates fragments of 156 and 70 base pairs while allele 2 generates a single 226 bp fragment.

The marker may be identified by any method known to one of ordinary skill in the art which identifies the presence or absence of the particular allele or marker, including for example, single-strand conformation polymorphism analysis (SSCP), RFLP analysis, heteroduplex analysis, denaturing gradient gel electrophoresis, allelic PCR, temperature gradient electrophoresis, ligase chain reaction, direct sequencing, minisequencing, nucleic acid hybridization, and micro-array-type detection of the MC4R gene and examination for the polymorphic site. Yet another technique includes an Invader Assay which includes isothermic amplification that relies on a catalytic release of fluorescence. See Third Wave Technology at www.twt.com all of which are intended to be within the scope of the invention.

One or more additional restriction enzymes and/or probes and/or primers can be used. Additional enzymes, constructed probes, and primers can be determined by routine experimentation by those of ordinary skill in the art and are intended to be within the scope of the invention.

Other possible techniques include non-gel systems such as TaqMan™ (Perkin Elmer). In this system, oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e., there is a mismatch of some form, the cleavage of the dye does not take place. Thus, only if the nucleotide sequence of the oligonucleotide probe is completely complementary to the template molecule to which it is bound will quenching be removed. A reaction mix can contain two different probe sequences each designed against different alleles that might be present, thus, allowing the detection of both alleles in one reaction.

Though the use of RFLPs is one method of detecting the polymorphism, other methods known to one of ordinary skill in the art may be used. Such methods include ones that analyze the polymorphic gene product and detect polymorphisms by detecting the resulting differences in the gene product.

Though the preferred method of separating restriction fragments is gel electrophoresis, other alternative methods known to one skilled in the art may be used to separate and determine the size of the restriction fragments.

It is possible to indirectly select for the polymorphism with alternative DNA markers and these methods are also within the scope of the invention. One can establish a linkage between specific alleles of alternative DNA markers and alleles of DNA markers known to be associated with the MC4R gene which have previously been shown to be associated with a particular trait. Examples of markers on the published PiGMaP chromosome map which are linked to the MC4R gene include S0331, BHT0433, and S0313. This is also true for other species as well, for example in human the MC4R gene is located at chromosome 18q21.3-q22.

The reagents suitable for applying the methods of the present invention may be packaged into convenient kits. The kits provide the necessary materials, packaged into suitable containers. At a minimum, the kit contains a reagent that identifies the polymorphism in the MC4R gene that is associated with the trait of meat quality. Preferably, the reagent that identifies the polymorphism is a PCR set (a set of primers, DNA polymerase, and four nucleoside triphosphates) that hybridize with the MC4R gene or a fragment thereof. Preferably, the PCR set and restriction enzyme that cleaves the MC4R sequence in at least one place are included in the kit. Preferably, the kit further comprises additional means, such as buffers or reagents, for detecting or measuring the detectable entity or providing a control. Other reagents used for hybridization, prehybridization, DNA extraction, visualization, and similar purposes may also be included, if desired.

The genetic markers, methods, and kits of the invention are useful in a breeding program to identify and/or to select for meat characteristics in a breed, line, or population of animals. Continuous selection and breeding of animals that are at least heterozygous and preferably homozygous for the desired polymorphism associated with the particular trait would lead to a breed, line, or population having those desired traits. Thus, the marker is a selection tool.

The following examples are offered to illustrate, but not limit the invention.

EXAMPLE 1

Melanocortin 4 Receptor PCR-RFLP Test—TaqI Polymorphism and Genetic Linkage Mapping of MC4R Gene Primers:

Primers were designed from homologous regions of human and rat MC4R sequences (Genbank Accession No. s77415 and u67863, respectively). These primers were used to amplify a 750-bp sequence of the porcine MC4R gene.

```
MC4R1:
5'TGG CAA TAG CCA AGA ACA AG 3'    (SEQ ID NO:5)

MC4R4:
5'CAG GGG ATA GCA ACA GAT GA 3'    (SEQ ID NO:6)
```

| PCR Conditions: | | |
|---|---|---|
| Mix 1: | 10 × Promega Buffer | 1.0 µL |
| | 25 mM MgCl₂ | 0.6 µL |
| | dNTPs mix (2.5 mM each) | 0.5 µL |
| | 25 pmol/µL MC4R1 | 0.1 µL |
| | 25 pmol/µL MC4R4 | 0.1 µL |
| | dd sterile H₂O | 7.5 µL |
| | Taq Polymerase (5 U/µL) | 0.07 µL |
| | Genomic DNA (12.5 ng/µL) | 1.0 µL |

Ten µL of Mix 1 and DNA were combined in reaction tube, then overlaid with mineral oil. The following PCR program was run: 94° C. for 2 min.; 35 cycles of 94° C. for 30 sec.; 58° C. 1 min., and 72° C. 1 min. 30 sec.; followed by a final extension at 72° C. for 15 min.

Five µl of the PCR reaction product was checked on a standard 1% agarose gel to confirm amplification success and clean negative control. Product size is approximately 750 base pairs. Digestion was performed by the following procedure.

| TaqI Digestion Reaction | 10 µL reaction |
|---|---|
| PCR product | 5.0 µL |
| 10 × TaqI NE Buffer | 1.0 µL |
| BSA (10 mg/ml) | 0.1 µL |
| TaqI enzyme (20 U/µL) | 0.5 µL |
| dd sterile H₂O | 3.4 µL |

A cocktail of the buffer, enzyme, BSA, and water was made. Five µL was added to each reaction tube containing the DNA. The mixture was then incubated at 65° C. for at least 4 hours to overnight. Loading dye was mixed with the digestion reaction and the total volume was loaded on a 3% agarose gel. The major bands for allele 1 are about 466, 225, and 76 bp. The allele 2 genotype bands are 542 and 225 bp. The heterozygote genotype has both allele 1 and allele 2.

Results

The amplified PCR product is about 750 bp. The sequence of the PCR product confirmed that the PCR product is MC4R gene with 97.6%, and 92.2% identities at the amino acid and DNA level, respectively, to corresponding human sequences. (see FIGS. 2 and 3).

The TaqI digestion of the PCR product produced allelic fragments of 466, 225, and 76 bp (allele 1), or 542 and 225 bp (allele 2). The heterozygote genotype has both types of alleles. Mendelian inheritance was observed in three three-generation international reference families, which were used to map this gene by linkage analysis.

The polymorphism between allele 1 and allele 2 resulting from a G→A transition at position 678 of the PCR product revealed a missense mutation of Aspartic acid codon (GAU) into Asparagine codon (AAU) at position 298 amino acid of MC4R protein. (See FIG. 1, SEQ ID NO:1).

Allele frequencies were determined by genotyping of DNA samples from a small number of animals from different breeds (Table 1). Allele 1 was observed with a frequency of 1 in Meishan, but was not observed or observed at very low frequency in Hampshire and Yorkshire. The frequencies of allele 1 in Landrace and Chester White were 0.5, respectively.

FIGS. 2 and 3 illustrate the differences between the DNA and amino acid sequences of the human and porcine MC4R gene (SEQ ID NOS:1-4).

TABLE 1

The Frequency of Allele 1 in Different Pig Breeds

| Breed | # Animals | Freq. Allele 1 |
| --- | --- | --- |
| Meishan | 8 | 1 |
| Large White | 8 | 0.56 |
| Yorkshire | 6 | 0.08 |
| Hampshire | 5 | 0 |
| Landrace | 4 | 0.5 |
| Chester White | 4 | 0.5 |
| Minzu | 2 | 1 |
| Wild Boar | 2 | 1 |

Linkage Analyses

Two-point and multi-point linkage analyses were performed on the genotypes of international reference families. See FIGS. 4a-4c. The data were analyzed by using the CRI-MAP program. MC4R was significantly linked to several markers on porcine chromosome (SSC) 1. The most closely linked markers (recombination fraction and LOD score in parentheses) are S0331 (0.02, 21.97), BHT0433 (0.02, 21.32), and S0313 (0.00, 17.76) by two-point linkage analysis. A multi-point linkage analysis produced the best map order of markers and MC4R (with distance in Kosambi cM): KGF-5.8-CAPN3-2.5-MEF2A-6.1-MC4R-5.6-S0313.

Somatic cell hybrid panel of pig and rodent was used to assign MC4R to a cytogenetic region. PCR products from pig specific primers were amplified in clones 7, 8, 16, 18, and 19. MC4R was localized to SSC1q 22-27.

EXAMPLE 2

Discovery of a Missense Variant of the Porcine Melanocortin-4 Receptor (MC4R) Gene To determine if there was an association of this MC4R polymorphism with phenotypic variation the mutation was tested in a large number of individual animals from several different pig lines. Analyses of growth and performance test records showed significant associations of MC4R genotypes with backfat, growth rate and feed intake in a number of lines. It is probable that the variant amino acid residue of the MC4R mutation causes a significant change of the MC4R function. These results support the functional significance of a pig MC4R missense mutation and suggest that comparative genomics based on model species may be equally important for application to farm animals as they are for human medicine.

Identification of mutations in the leptin and the leptin receptor has provided some information on genetic components involved in the regulation of energy balance (Zhang et al. 1994; Tartaglia et al. 1995). Genetic studies using animal models have facilitated the identification of major genetic causes of obesity (Andersson 1996; Pomp 1997; Giridharan 1998). Furthermore, several other genes involved in the neural signaling pathway of energy homeostasis have been identified (Flier and Maratos-Flier 1998; Schwartz et al. 1999). Of particular interest among candidate signaling molecules involved in the regulation of energy homeostasis is the melanocortin-4 receptor (MC4R). The MC4R response to leptin signaling is a link between food intake and body weight (Seeley et al. 1997; Marsh et al. 1999). Neuropeptide Y (NPY) signaling in the central nervous system is also mediated by the MC4R protein (Kask et al. 1998). Several mutations in MC4R including frameshift and nonsense mutations are associated with dominantly inherited obesity in humans (Vaisse et al. 1998; Yeo et al. 1998). Some other MC4R missense mutations in humans have also been identified (Gotoda et al. 1997; Hinney et al. 1999) but the functional significance of these mutations has not been characterized.

Selection based on growth characteristics has been of great importance to the pig industry because of costs associated with feeding and consumer preference for lean meat. Efficient genetic improvement in these quantitative traits may be augmented through the use of marker assisted selection (MAS) using high density genetic maps (Dekkers and van Arendonk 1998; Rothschild and Plastow 1999). An important tool in this process is comparative mapping using the well-developed human and mouse gene maps, which assist in the identification of corresponding genomic regions or major genes controlling growth and performance traits in the pig. Biological understanding of complex traits in human or model species offers an alternative approach to identify genes responsible for the traits of economic interest in livestock. Several quantitative trait loci (QTL) linkage scans using phenotypically divergent breeds and candidate gene analyses have been successfully conducted for fatness and growth traits (Yu et al. 1995; Casas-Carrillo et al. 1997; Knorr et al. 1997; Knott et al. 1998; Rohrer et al. 1998; Wang et al. 1998; Paszek et al. 1999), but no individual genes with major effects on growth and performance traits have yet been established for commercial populations. The role of MC4R in feed intake and obesity suggests it may be an important genetic marker for the growth-related traits in the pig.

Materials and Methods

Animals. Pigs were raised under normal production conditions under the care of PIC employees in nucleus farms in the United States and Europe.

PCR amplification of a pig MC4R gene fragment. Primers were designed from homologous regions of human and rat MC4R sequences (GenBank accession no. s77415 and u67863, respectively). The primers were: forward primer: 5'-TGG CAA TAG CCA AGA ACA AG-3' (SEQ ID NO:5) and reverse primer: 5'-CAG GGG ATA GCA ACA GAT GA-3' (SEQ ID NO:6). The PCR reaction was performed using 12.5 ng of porcine genomic DNA, 1×PCR buffer, 1.5 mM MgCl$_2$, 0.125 mM dNTPs, 0.3 mM of each primer, and 0.35 U Taq DNA polymerase (Promega) in a 10 µL final volume. The conditions for PCR were as follows: 2 min at 94° C.; 35 cycles of 30 s at 94° C., 1 min at 56° C., 1 min 30 s at 92° C., and a final 15 min extension at 72° C. in a Robocycler (Stratagene, La Jolla, Calif.).

Sequencing and mutation detection. Sequencing of the PCR products from several individual pigs of different breeds was conducted and the sequences were compared to detect any nucleotide change. Sequencing was performed on an ABI sequencer 377 (Applied Biosystems). The porcine MC4R sequence has been submitted to GenBank, and has accession number AE087937. The sequence analysis revealed one nucleotide substitution situated within a TaqI restriction enzyme recognition site (Kim et al. 1999). A set of primers was then designed to generate a smaller MC4R gene fragment, which contained only one informative Taqi restriction site to specify the polymorphic site and to facilitate the PCR-RFLP test. These primers were: forward 5'-TAC CCT GAC CAT CTT GAT TG-3' (SEQ ID NO:9) and reverse: 5'-ATA GCA ACA GAT GAT CTC TTT G-3' (SEQ ID NO:10).

Results

Identification of a missense mutation in the pig MC4R gene. The MC4R gene consists of approximately 1 kb of coding sequence contained within a single exon. About 750 bp of a pig MC4R gene fragment was produced by PCR (Kim et al. 1999). The sequence of the PCR product confirmed that the PCR product is the MC4R gene with 92.2% and 97.6% identities at nucleotide and the amino acid levels, respectively, to the human MC4R sequence. Multiple alignments of the sequences from individual animals of several breeds identified a single nucleotide substitution (G→A; FIG. 5). The polymorphism revealed a missense mutation that replaces aspartic acid (GAU) with asparagine (AAU) at the position identical to amino acid 298 of human MC4R protein. To confirm this base change, we designed pig-specific primers flanking the polymorphic site and analyzed the polymorphism as a TaqI PCR-RFLP gel (FIG. 6). FIG. 6 shows a TaqI digestion of the PCR product analyzed by agarose-gel electrophoresis. Allele 1 produced 156 and 70 bp fragments and allele 2 produced a 226 bp fragment as the PCR-RFLP. The heterozygote has both allele 1 and 2 fragments. Molecular marker (M) and MC4R genotypes are indicated at the top of each lane.

The MC4R missense mutation is within a highly conserved region among melanocortin receptors (MCR). The MCR is a subfamily of G-protein coupled receptors (GPCR) containing certain conserved structural elements common to most other GPCRs, but overall amino acid identities between MCR and other GPCRs are low (Tatro 1996). A multiple-alignment of the predicted amino acid sequences of the pig MC4R with MC4R proteins from other species, other MCR proteins, or representative GPCRs showed that the aspartic acid found at position 298 of the seventh transmembrane domain is very highly conserved in the MCR proteins (FIG. 7). It is interesting to note, however, that this position is occupied by asparagine in most other GPCRs. The MCR proteins show 40-80% amino acid identity with each other (Tatro 1996), but the second intracytoplasmic loop and the seventh transmembrane domain are highly conserved among MCR proteins (Gantz et al. 1993). Some of the relationships between MCR structure and function have been discovered by the studies of natural and experimental mutations in humans and mice (Robbins et al. 1993; Valverde et al. 1995; Frandberg et al. 1998). These studies indicate that some mutations in highly conserved regions cause structural changes and alter the function of the receptor. The Asp298Asn substitution mutation could have an effect on the function of the receptor. However, this will require further testing but it is known that change of the homologous residue in MClR (Asp294His) is associated with fair skin and red hair in humans (Valverde et al. 1995).

EXAMPLE 3

Quantity and quality are descriptive terms of great importance in the meat industry. As the live animal is converted to meat and the meat moves along the line of distribution, from slaughters and processors to retailers and finally to consumers, the factor of quality becomes increasingly more important. Obviously, economic considerations influence the concerns for quantity and quality.

The condition of pale, soft and exudative (PSE) pork and generally very high variability of pork quality was recognized and documented by 1960, and both quality "defects" have been viewed as having less value for further processing and being inferior for consumers. Although an enormous amount of research has been directed at the problem through a half-century of effort, surveys of incidence showed, in pork produced in the U.S.A., that 18% was of inferior quality (PSE) in 1963 and 16% in 1992. Thus, the existence of gene markers associated with both the ability to change the levels of traits (i.e. meat color, water holding capacity, tenderness or marbling) as well as to reduce variation in meat quality characteristics provides excellent opportunities for a dramatic improvement in meat quality. First, gene markers allow for significant steps to be made in the desired direction of quality traits; (e.g. improving technological yield of processed ham and reducing moisture (purge) losses of fresh ham and loins, by selecting against the RN gene in pigs). Secondly, gene markers will help reduce meat quality variation, since we can fix relevant genes in the breeding populations.

Meat quality is typically measured in slaughter plants in terms of the pH of the meat, color (using several different instruments and methods e.g. Minolta, [Min]), marbling and drip loss.

For example, the following descriptions of desirable meat quality characteristics are generally accepted by the industry based on their economic value at different segments of the pork supply chain:

Loin Minolta Lightness (L*): The range of 43-47 units (from darker to lighter color) is acceptable, but L* of 43 is better; i.e., has higher economic value, in general in this range**

Loin Japanese Color Score (JCS): The range of 2.5-5.0 units (from lighter to darker color) is acceptable, but JCS of 3-4 is better Loin Marbling (level of intramuscular fat): Generally, higher marbling is better as it is associated with improved meat eating quality characteristics Loin pHu: (ultimate meat acidity measured 24 hours post-mortem; this attribute is the single most important trait of pork quality);—The range of 5.50-5-80 is desirable, but 5.80 is better as it positively influences the color and (low) purge of the meat Ham Minolta lightness (L*) The range of 43-52 units is acceptable, but lower (43) is better Ham pHu: higher; i.e., 5.80, is better Drip loss or purge: the range of 1%-3% is acceptable, but lower is better

**this may be dependent upon market, for example in Japan darker pork is preferred. Sosnicki, A. A., E. R. Wilson, E.

B. Sheiss, A. devries, 1998 "Is there a cost effective way to produce high quality pork?", *Reciprocal Meat Conference Proceedings*, Vol. 51.

Results

TABLE 2

Least square means for different MC4R genotypic classes based on a sample of 1146 animals from six genetic lines (preferred class in bold)

| Trait | Genotype | | | p value |
| --- | --- | --- | --- | --- |
| | 11 | 12 | 22 | |
| Loin pHu | 5.70 | 5.70 | 5.73 | <0.01 |
| Ham pHu | 5.69 | 5.69 | 5.72 | <0.07 |
| Ham Min L | 48.44 | 48.39 | 47.38 | <0.03 |
| Drip | 2.29 | 2.43 | 2.10 | <0.07 |
| Loin Marbling | 2.17 | 2.18 | 2.25 | <0.42 |
| Days to 110 g* | 169.2 | 168.5 | 166.4 | <0.0001 |

*The samples size for Days was 2366

Significant effects of marker genotype are identified for ultimate pH (pHu), color (Min) and drip loss and a desirable trend is observed for marbling. The size of the effects observed between genotypes while small are of commercial significance in terms of differences in meat quality. It can be seen from the results in Table 2 that allele 2 is the preferred allele in this sample for all four meat quality measures. Interestingly, this is the preferred allele for growth as reported in WO 00/06777. This is a particularly important finding, as it is somewhat unexpected. In general, there is a negative correlation between growth rate and meat quality. Indeed, there is a general perception that meat quality has decreased as breeders have selected for increased growth rate.

In some situations we might anticipate that the associations between the marker genotype and the traits may differ in direction. This will be the case where the marker utilized here is linked to the polymorphism or gene that is causing the effect. In this situation, the MC4R marker will still have utility, once the association has been identified by experimentation.

The traits measured here are only some of the measures that may be used for determining meat quality. Many others can be used that are correlated to these measures. Thus it will be expected that similar effects will be observed for such economically important traits as water holding and binding capacity, curing and cooking yields and that these traits and that these will also extend to related measures of eating quality such as tenderness, juiciness, flavor and taste. See Sosnicki, supra.

The present invention concerns the identification of significant associations between the MC4R marker genotype and meat quality. It will be realized by those skilled in the art that other gene markers located in this region of the swine genome (swine chromosome 1) will also be suitable for marker assisted selection of these traits.

EXAMPLE 4

A total of 257 animals from a Pietrain-based line of pigs were slaughtered and meat quality characteristics determined at the time of slaughter and during post-slaughter handling/conditioning for meat production. MC4R genotypes were determined using methods disclosed herein. Associations between marker genotype and MQ traits were then calculated. The results are depicted in Table 3.

Significant associations were obtained for ultimate pH and color (Minolta L) of the ham. Hams from animals of genotype 2,2 will be preferred in markets which favor these characteristics.

The association can be used to select the parents of slaughter pigs or to improve breeding stock by within line selection. Alternatively, ham processors may chose to purchase pigs of the preferred genotype in order to improve the overall quality of the product (2,2 carcasses will be a better color and will be expected to provide greater yield than those from 1,1 or 1,2 animals). In addition, by selecting a single genotype they will also reduce the variation in product quality due to the different MC4R genotypes.

TABLE 3

MC4R genotype and Ham pHu and Min L for a Pietrain based line selected to be free of the Halothane gene

| Genotype | n | pHu | Min L |
| --- | --- | --- | --- |
| 11 | 119 | 5.72 | 49.70 |
| 12 | 101 | 5.73 | 50.03 |
| 22 | 37 | 5.80 | 47.83 |
| p | | <0.04 | <0.09 |

The present invention describes an association between MC4R genotype and meat quality characteristics such as pH, color and marbling in the pig. These traits are in turn associated with visual appearance and processing and eating quality characteristics such as tenderness.

These traits also describe meat quality in other species such as beef and lamb. Because of the relatively close evolutionary link between pigs and other meat species it can be predicted that variation in this gene is also likely to be associated with meat quality (MQ) in these other species. Polymorphisms can be identified in the MC4R gene of these species using the same approach set out here and the resulting SNPs used for association analysis.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

The following citations are hereby incorporated in their entirety by reference:

Andersson L B (1996), *Ann Med.*, 28:5-7.
Arden K C (1990), *Cytogenet. Cell Genet.* 53:161-165.
Barinaga M (1996), *Science* 271:913.
Bray G A (1978). *Physiol. Rev.* 59, 719-809.
Casas-Carillo E (1997), *J Anim Sci* 75:2047-2053.
Chajlani V, *Biochem. Biophys. Res. Commun.*, 195, 866-873.
Chen H (1995), *Cell* 84, 491-495.
Chua S C (1996). *Science* 271, 994-996.
Chung W K (1996). *Genome Res.* 6, 431-438.
Cioffi J A (1996). *Nature Med.* 2, 585-589.
Cybulsky M I (1991), *Proc. Nat. Acad. Sci.* 88:7859-7863.
Dekkers J C M (1998), *Genet Res* 71:257-275.
Flier J S (1998), *Cell* 92:437-440.

Frandberg P (1997), *Biochem Biophys Res Commun* 236: 489-492.
Frankel W N (1996), *Nat Genet* 14:371-373.
Gantz (1993), *J. Biol. Chem.* 268, 15174-15179.
Gantz (1994), *Biochem. Biophys. Res. Comm.*, 200, 1214-1220.
Gantz I (1993a), *J. Biol. Chem.* 268, 8246-8250.
Giridharan N V (1998), *Indian J Med res* 108:225-242.
Gotoda T (1997), *Diabetologia* 40:976-979.
Goureau A (1996). *Genomics*.36:252-262.
Griffon N (1994), *Biochem. Biophys. Res. Comm.*, 200, 1007-1014.
Helm J (1994), *J. Anim. Science* 72:2764.
Hinney A (1999), *J Clin Endocrinol Metab* 84:1483-1486.
Huszar (1997), *Cell* 88:131-141.
Kask A (1998), *Biochem Biophys Res Commun* 248:245-249.
Kim K S (2000), *J Anim Sci* 78:791-792.
Knorr C (1997), *Anim Genet* 28:124-128.
Knott S A (1998), *Genetics* 149:1069-1680.
Labbe 0 (1994), *Biochemistry,* 33, 4543-4549.
Lee G H (1996), *Nature* 379, 632-635.
Lu Dongsi (1994), *Nature:*371:799-802
Marsh D J (1999), *Nat Genet* 21:119-122.
Meuwissen, T. H. E. and Goddard, M. E. (1996) "The use of Marker Haplotypes in Animal Breeding Schemes", Genet. Sel. Evol., 28 161-176
Montjoy K G (1992), *Science* 257, 1248-1251.
Montjoy K G (1994), *Mol. Endocrinol.* 8, 1298-1308.
Paszek A (1996), *Proceed. Midwest. ASAS Meeting*, p. 24.
Paszek A A (1999), *Mamm Genome* 10:117-122.
Phillips M (1996), *Nature Genetics* 13:18-19.
Pomp D (1997), *Behav Genet* 27:285-306.
Robbins L S (1993), *Cell* 72:827-834.
Robic A (1996), *Mamm. Genome* 7, 438-445.
Rohrer G A (1998), *J Anim Sci* 76:2247-2254.
Rothschild M F (1996), *PNAS* 93: 201-205.
Rothschild M F (1999), *AgBiotechNet* 1:1-8.
Schwartz M W (1999), *Am J Clin Nutr* 69:584-96.
Seeley R J (1997), *Nature* 390:349.
Tartaglia L A (1995), *Cell* 83:1263-1271.
Tatro J B (1996), *Neuroimmunomodulation* 3:259-284.
Truett G E (1995), *Mamm. Genome* 6, 25-30.
Vaisse C (1998), *Nat Genet* 20:113-114.
Valverde P (1995), *Nat Genet* 11:328-330.
Wang L (1998), *J Anim Sci* 76:2560-2567.
Warner C M (1991), *Immunogenetics of the MHC*, VCH Publishers, NY, N.Y., pp. 368-397.
Winick J D (1996), *Genomics* 36, 221-222.
Xy Y (1994), *Biol. Reprod.* 51:695-699.
Yeo G S (1998), *Nat Genet* 20:111-112.
Yerle M (1996), *Cytogenet. Cell Genet.* 73, 194-202.
Youngs C R (1993), *J. Anim. Sci.,* 1561-1565.
Yu T P (1995), *J Anim Sci* 73:1282-1288.
Zhang Y (1994), *Nature* 372:425-432.
Ziang Z H (1999), *Mamm Genome* 12:191-193.

---

What is claimed is:

1. A method of identifying a pig which possesses a genotype indicative of the phenotypes increased pH, decreased Minolta, decreased drip loss, and increased rate of weight gain, wherein a pig homozygous for adenine at position 678 of SEQ ID NO:1 is indicative of said pig being more likely to have one or more of the phenotypes than a pig with a guanine at position 678 of SEQ ID NO:1, wherein the increase or decrease is relative to a pig having guanine at position 678 of SEQ ID NO:1, said method comprising directly detecting the nucleotide present at position 678 of SEQ ID NO:1 in both alleles of the pig's MC4R gene to determine the pig's genotype, and relating the genotype to the phenotype.

* * * * *

SEQUENCE LISTING

<160> NUMBER OF SEQ ID NOS: 26

<210> SEQ ID NO 1
<211> LENGTH: 746
<212> TYPE: DNA
<213> ORGANISM: Sus scrofa

<400> SEQUENCE: 1

```
acaagaatct gcattcaccc atgtactttt tcatctgtag cctggctgtg gctgatatgc      60
tggtgagcgt ttccaatggg tcagaaacca ttgtcatcac cctattaaac agcacggaca     120
cggacgcaca gagtttcaca gtgaatattg ataatgtcat tgactcagtg atctgtagct     180
ccttactcgc ctcaatttgc agcctgcttt cgattgcagt ggacaggtat tttactatct     240
tttatgctct ccagtaccat aacattatga cagttaagcg ggttggaatc atcatcagtt     300
gtatctgggc agtctgcacg gtgtcgggtg ttttgttcat catttactca gatagcagtg     360
ctgttattat ctgcctcata accgtgttct tcaccatgct ggctctcatg gcttctctct     420
atgtccacat gttcctcatg gccagactcc acattaagag gatcgccgtc ctcccaggca     480
ctggcaccat ccgccaaggt gccaacatga agggggcaat taccctgacc atcttgattg     540
gggtctttgt ggtctgctgg gccccttct tcctccactt aatattctat atctcctgcc      600
cccagaatcc atactgtgtg tgcttcatgt ctcactttaa tttgtatctc atcctgatca     660
tgtgtaattc catcatcrat cccctgattt atgcactccg gagccaagaa ctgaggaaaa     720
ccttcaaaga gatcatctgt tgctat                                          746
```

<210> SEQ ID NO 2
<211> LENGTH: 840
<212> TYPE: DNA
<213> ORGANISM: Homo sapiens

<400> SEQUENCE: 2

```
atatcttagt gattgtggca atagccaaga acaagaatct gcattcaccc atgtactttt     60
tcatctgcag cttggctgtg gctgatatgc tggtgagcgt ttcaaatgga tcagaaacca    120
ttatcatcac cctattaaac agtacagata cggatgcaca gagtttcaca gtgaatattg    180
ataatgtcat tgactcggtg atctgtagct ccttgcttgc atccatttgc agcctgcttt    240
caattgcagt ggacaggtac tttactatct tctatgctct ccagtaccat aacattatga    300
cagttaagcg ggttgggatc agcataagtt gtatctgggc agcttgcacg gtttcaggca    360
ttttgttcat catttactca gatagtagtg ctgtcatcat ctgcctcatc accatgttct    420
tcaccatgct ggctctcatg gcttctctct atgtccacat gttcctgatg ccaggcttc    480
acattaagag gattgctgtc ctccccggca ctggtgccat ccgccaaggt gccaatatga    540
agggagcgat taccttgacc atcctgattg gcgtctttgt tgtctgctgg gccccattct    600
tcctccactt aatattctac atctcttgtc ctcagaatcc atattgtgtg tgcttcatgt    660
ctcactttaa cttgtatctc atactgatca tgtgtaattc aatcatcgat cctctgattt    720
atgcactccg gagtcaagaa ctgaggaaaa ccttcaaaga gatcatctgt tgctatcccc    780
tgggaggcct tgtgacttg tctagcagat attaaatggg gacagagcac gcaatatagg    840
```

<210> SEQ ID NO 3
<211> LENGTH: 311
<212> TYPE: PRT
<213> ORGANISM: Homo sapiens
<220> FEATURE:
<221> NAME/KEY: misc_feature
<222> LOCATION: (298)..(298)
<223> OTHER INFORMATION: "Xaa" can be any amino acid

<400> SEQUENCE: 3

Gln Leu Phe Val Ser Pro Glu Val Phe Val Thr Leu Gly Val Ile Ser
1               5                   10                  15

Leu Leu Glu Asn Ile Leu Val Ile Val Ala Ile Ala Lys Asn Lys Asn
            20                  25                  30

Leu His Ser Pro Met Tyr Phe Phe Ile Cys Ser Leu Ala Val Ala Asp
        35                  40                  45

Met Leu Val Ser Val Ser Asn Gly Ser Glu Thr Ile Ile Ile Thr Leu
    50                  55                  60

Leu Asn Ser Thr Asp Thr Asp Ala Gln Ser Phe Thr Val Asn Ile Asp
65                  70                  75                  80

Asn Val Ile Asp Ser Val Ile Cys Ser Ser Leu Leu Ala Ser Ile Cys
                85                  90                  95

Ser Leu Leu Ser Ile Ala Val Asp Arg Tyr Phe Thr Ile Phe Tyr Ala
            100                 105                 110

Leu Gln Tyr His Asn Ile Met Thr Val Lys Arg Val Gly Ile Ser Ile
        115                 120                 125

Ser Cys Ile Trp Ala Ala Cys Thr Val Ser Gly Ile Leu Phe Ile Ile
    130                 135                 140

Tyr Ser Asp Ser Ser Ala Val Ile Ile Cys Leu Ile Thr Met Phe Phe
145                 150                 155                 160

Thr Met Leu Ala Leu Met Ala Ser Leu Tyr Val His Met Phe Leu Met
                165                 170                 175

Ala Arg Leu His Ile Lys Arg Ile Ala Val Leu Pro Gly Thr Gly Ala
            180                 185                 190

-continued

```
Ile Arg Gln Gly Ala Asn Met Lys Gly Ala Ile Thr Leu Thr Ile Leu
            195                 200                 205

Ile Gly Val Phe Val Val Cys Trp Ala Pro Phe Phe Leu His Leu Ile
210                 215                 220

Phe Tyr Ile Ser Cys Pro Gln Asn Pro Tyr Cys Val Cys Phe Met Ser
225                 230                 235                 240

His Phe Asn Leu Tyr Leu Ile Leu Ile Met Cys Asn Ser Ile Ile Asp
                245                 250                 255

Pro Leu Ile Tyr Ala Leu Arg Ser Gln Glu Leu Arg Lys Thr Phe Lys
            260                 265                 270

Glu Ile Ile Cys Cys Tyr Pro Leu Gly Gly Leu Cys Asp Leu Ser Ser
            275                 280                 285

Arg Tyr Ala Pro Pro Glu Asn Asp Ile Xaa Val Ile Cys Asn Phe Ile
            290                 295                 300

Asp Glu Asn Thr Ile Ala Leu
305                 310

<210> SEQ ID NO 4
<211> LENGTH: 248
<212> TYPE: PRT
<213> ORGANISM: Homo sapiens

<400> SEQUENCE: 4

Lys Asn Leu His Ser Pro Met Tyr Phe Phe Ile Cys Ser Leu Ala Val
1               5                   10                  15

Ala Asp Met Leu Val Ser Val Ser Asn Gly Ser Glu Thr Ile Val Ile
            20                  25                  30

Thr Leu Leu Asn Ser Thr Asp Thr Asp Ala Gln Ser Phe Thr Val Asn
            35                  40                  45

Ile Asp Asn Val Ile Asp Ser Val Ile Cys Ser Ser Leu Leu Ala Ser
        50                  55                  60

Ile Cys Ser Leu Leu Ser Ile Ala Val Asp Arg Tyr Phe Thr Ile Phe
65                  70                  75                  80

Tyr Ala Leu Gln Tyr His Asn Ile Met Thr Val Lys Arg Val Gly Ile
                85                  90                  95

Ile Ile Ser Cys Ile Trp Ala Val Cys Thr Val Ser Gly Val Leu Phe
            100                 105                 110

Ile Ile Tyr Ser Asp Ser Ser Ala Val Ile Ile Cys Leu Ile Thr Val
            115                 120                 125

Phe Phe Thr Met Leu Ala Leu Met Ala Ser Leu Tyr Val His Met Phe
130                 135                 140

Leu Met Ala Arg Leu His Ile Lys Arg Ile Ala Val Leu Pro Gly Thr
145                 150                 155                 160

Gly Thr Ile Arg Gln Gly Ala Asn Met Lys Gly Ala Ile Thr Leu Thr
                165                 170                 175

Ile Leu Ile Gly Val Phe Val Val Cys Trp Ala Pro Phe Phe Leu His
            180                 185                 190

Leu Ile Phe Tyr Ile Ser Cys Pro Gln Asn Pro Tyr Cys Val Cys Phe
        195                 200                 205

Met Ser His Phe Asn Leu Tyr Leu Ile Leu Ile Met Cys Asn Ser Ile
    210                 215                 220

Ile Asn Pro Leu Ile Tyr Ala Leu Arg Ser Gln Glu Leu Arg Lys Thr
225                 230                 235                 240

Phe Lys Glu Ile Ile Cys Cys Tyr
                245
```

```
<210> SEQ ID NO 5
<211> LENGTH: 20
<212> TYPE: DNA
<213> ORGANISM: Sus scrofa

<400> SEQUENCE: 5
tggcaatagc caagaacaag                                                  20

<210> SEQ ID NO 6
<211> LENGTH: 20
<212> TYPE: DNA
<213> ORGANISM: Sus scrofa

<400> SEQUENCE: 6 cagggatag caacagatga                                                   20

<210> SEQ ID NO 7
<211> LENGTH: 18
<212> TYPE: DNA
<213> ORGANISM: Sus scrofa

<400> SEQUENCE: 7
ttaagtggag gaagaagg                                                    18

<210> SEQ ID NO 8
<211> LENGTH: 19
<212> TYPE: DNA
<213> ORGANISM: Sus scrofa

<400> SEQUENCE: 8
cattatgaca gttaagcgg                                                   19

<210> SEQ ID NO 9
<211> LENGTH: 20
<212> TYPE: DNA
<213> ORGANISM: Sus scrofa

<400> SEQUENCE: 9
taccctgacc atcttgattg                                                  20

<210> SEQ ID NO 10
<211> LENGTH: 22
<212> TYPE: DNA
<213> ORGANISM: Sus scrofa

<400> SEQUENCE: 10
atagcaacag atgatctctt tg                                               22

<210> SEQ ID NO 11
<211> LENGTH: 24
<212> TYPE: PRT
<213> ORGANISM: Sus scrofa

<400> SEQUENCE: 11

Met Ser His Phe Asn Leu Tyr Leu Ile Leu Ile Met Cys Asn Ser Ile
1               5                   10                  15

Ile Asp Pro Leu Ile Tyr Ala Leu
            20

<210> SEQ ID NO 12
<211> LENGTH: 24
<212> TYPE: PRT
```

<213> ORGANISM: Homo sapiens

<400> SEQUENCE: 12

Met Ser His Phe Asn Leu Tyr Leu Ile Leu Ile Met Cys Asn Ser Ile
1               5                   10                  15

Ile Asp Pro Leu Ile Tyr Ala Leu
            20

<210> SEQ ID NO 13
<211> LENGTH: 24
<212> TYPE: PRT
<213> ORGANISM: Rattus norvegicus

<400> SEQUENCE: 13

Met Ser His Phe Asn Leu Tyr Leu Ile Leu Ile Met Cys Asn Ala Val
1               5                   10                  15

Ile Asp Pro Leu Ile Tyr Ala Leu
            20

<210> SEQ ID NO 14
<211> LENGTH: 23
<212> TYPE: PRT
<213> ORGANISM: Homo sapiens

<400> SEQUENCE: 14

Met Ser His Phe Asn Met Tyr Leu Ile Leu Ile Met Cys Asn Ser Val
1               5                   10                  15

Ile Asp Pro Leu Ile Tyr Ala
            20

<210> SEQ ID NO 15
<211> LENGTH: 23
<212> TYPE: PRT
<213> ORGANISM: Mammalia sp.

<400> SEQUENCE: 15

Met Ser His Phe Asn Met Tyr Leu Ile Leu Ile Met Cys Asn Ser Val
1               5                   10                  15

Ile Asp Pro Leu Ile Tyr Ala
            20

<210> SEQ ID NO 16
<211> LENGTH: 24
<212> TYPE: PRT
<213> ORGANISM: Homo sapiens

<400> SEQUENCE: 16

Met Ser Leu Phe Gln Val Asn Gly Val Leu Ile Met Cys Asn Ala Ile
1               5                   10                  15

Ile Asp Pro Phe Ile Tyr Ala Leu
            20

<210> SEQ ID NO 17
<211> LENGTH: 22
<212> TYPE: PRT
<213> ORGANISM: Bos taurus

<400> SEQUENCE: 17

Ala His Phe Asn Thr Tyr Leu Val Leu Ile Met Cys Asn Ser Val Ile
1               5                   10                  15

Asp Pro Leu Ile Tyr Ala
            20

<210> SEQ ID NO 18
<211> LENGTH: 22
<212> TYPE: PRT
<213> ORGANISM: Homo sapiens

<400> SEQUENCE: 18

Ala His Phe Asn Thr Tyr Leu Val Leu Ile Met Cys Asn Ser Val Ile
1               5                   10                  15

Asp Pro Leu Ile Tyr Ala
            20

<210> SEQ ID NO 19
<211> LENGTH: 23
<212> TYPE: PRT
<213> ORGANISM: Homo sapiens

<400> SEQUENCE: 19

Met Ser His Phe Asn Met Tyr Leu Ile Leu Ile Met Cys Asn Ser Val
1               5                   10                  15

Met Asp Pro Leu Ile Tyr Ala
            20

<210> SEQ ID NO 20
<211> LENGTH: 22
<212> TYPE: PRT
<213> ORGANISM: Homo sapiens

<400> SEQUENCE: 20

Ser Tyr Phe Asn Leu Phe Leu Ile Leu Ile Ile Cys Asn Ser Val Val
1               5                   10                  15

Asp Pro Leu Ile Tyr Ala
            20

<210> SEQ ID NO 21
<211> LENGTH: 25
<212> TYPE: PRT
<213> ORGANISM: Bos taurus

<400> SEQUENCE: 21

Leu Ala Tyr Glu Lys Phe Phe Leu Leu Leu Ala Glu Phe Asn Ser Ala
1               5                   10                  15

Met Asn Pro Ile Ile Tyr Ser Tyr Arg
            20                  25

<210> SEQ ID NO 22
<211> LENGTH: 19
<212> TYPE: PRT
<213> ORGANISM: Homo sapiens

<400> SEQUENCE: 22

Phe Leu Leu Leu Ala Glu Ala Asn Ser Leu Val Asn Ala Ala Val Tyr
1               5                   10                  15

Ser Cys Arg

<210> SEQ ID NO 23
<211> LENGTH: 22
<212> TYPE: PRT
<213> ORGANISM: Homo sapiens

<400> SEQUENCE: 23

Val Phe Ala Phe Cys Ser Met Leu Cys Leu Leu Asn Ser Thr Val Asn

```
                1               5              10             15

Pro Leu Ile Tyr Ala Leu
                20

<210> SEQ ID NO 24
<211> LENGTH: 21
<212> TYPE: PRT
<213> ORGANISM: Homo sapiens

<400> SEQUENCE: 24

Phe Gln Phe Phe Phe Trp Ile Gly Tyr Cys Asn Ser Ser Leu Asn Pro
1               5                  10                  15

Val Ile Tyr Thr Ile
                20

<210> SEQ ID NO 25
<211> LENGTH: 22
<212> TYPE: PRT
<213> ORGANISM: Rattus norvegicus

<400> SEQUENCE: 25

Phe Asp Phe Val Val Ile Leu Thr Tyr Ala Asn Ser Cys Ala Asn Pro
1               5                  10                  15

Ile Leu Tyr Ala Phe Leu
                20

<210> SEQ ID NO 26
<211> LENGTH: 16
<212> TYPE: PRT
<213> ORGANISM: Homo sapiens

<400> SEQUENCE: 26

Leu Ala Tyr Ser Asn Ser Ser Val Asn Pro Ile Ile Tyr Ala Phe Leu
1               5                  10                  15
```